US011220527B2

(12) United States Patent
Mazella et al.

(10) Patent No.: US 11,220,527 B2
(45) Date of Patent: Jan. 11, 2022

(54) PEPTIDES DERIVED FROM THE PROPEPTIDE NTSR3 AND THEIR USE IN THE TREATMENT OF DEPRESSION (71) Applicants: CENTRE NATIONAL DE LA RECHERCHE SCIENTIFIQUE, Paris (FR); UNIVERSITÉ DE NICE—SOPHIA ANTIPOLIS, Nice (FR)

(72) Inventors: Jean Mazella, biot (FR); Marc Borsotto, Grasse (FR); Catherine Heurteaux, La-Colle-sur-Loup (FR); Alaeddine Djillani, Setif (DZ); Sébastien Moreno, Vence (FR); Mariel Pietri, Ajaccio (FR)

(73) Assignees: CENTRE NATIONAL DE LA RECHERCHE SCIENTIFIQUE, Paris (FR); UNIVERSITÉ DE NICE SOPHIA ANTIPOLIS, Nice (FR)

(*) Notice: Subject to any disclaimer, the term of this patent is extended or adjusted under 35 U.S.C. 154(b) by 24 days.

(21) Appl. No.: 16/340,832

(22) PCT Filed: Oct. 11, 2017

(86) PCT No.: PCT/FR2017/052788
§ 371 (c)(1),
(2) Date: Apr. 10, 2019

(87) PCT Pub. No.: WO2018/069641
PCT Pub. Date: Apr. 19, 2018

(65) Prior Publication Data
US 2019/0270771 A1    Sep. 5, 2019

(30) Foreign Application Priority Data

Oct. 11, 2016 (FR) .................. 1659781
Mar. 16, 2017 (FR) .................. 1752162
May 11, 2017 (FR) .................. 1754127

(51) Int. Cl.
| *C07K 7/06* | (2006.01) |
| *A61P 25/24* | (2006.01) |
| *A61K 31/7105* | (2006.01) |
| *A61K 38/08* | (2019.01) |
| *C07K 7/08* | (2006.01) |
| *C07K 14/72* | (2006.01) |
| *A61K 38/10* | (2006.01) |
| *C07K 16/00* | (2006.01) |
| *C07K 14/435* | (2006.01) |
| *C07K 16/18* | (2006.01) |
| *A61K 38/00* | (2006.01) |
| *A61P 3/10* | (2006.01) |
| *A61P 25/08* | (2006.01) |
| *A61P 35/00* | (2006.01) |
| *C12N 15/63* | (2006.01) |
| *G01N 33/543* | (2006.01) |

(52) U.S. Cl.
CPC .............. *C07K 7/06* (2013.01); *A61K 31/7105* (2013.01); *A61K 38/08* (2013.01); *A61K 38/10* (2013.01); *A61P 3/10* (2018.01); *A61P 25/08* (2018.01); *A61P 25/24* (2018.01); *A61P 35/00* (2018.01); *C07K 7/08* (2013.01); *C07K 14/435* (2013.01); *C07K 14/723* (2013.01); *C07K 16/00* (2013.01); *C07K 16/18* (2013.01); *C12N 15/63* (2013.01); *G01N 33/54306* (2013.01); *A61K 38/00* (2013.01)

(58) Field of Classification Search
CPC .......... C07K 7/06; C07K 7/08; C07K 14/723; C07K 16/00; C07K 14/435; C07K 16/18; A61P 3/10; A61P 25/24; A61P 25/08; A61P 35/00; A61K 31/7105; A61K 38/08; A61K 38/10; A61K 38/00; C12N 15/63; G01N 33/54306
See application file for complete search history.

(56) References Cited

U.S. PATENT DOCUMENTS

| 8,066,997 B2 | 11/2011 | Nykjaer et al. |
| 8,252,748 B2 | 8/2012 | Mazella et al. |
| 8,815,808 B2 | 8/2014 | Nykjaer et al. |
| 8,986,690 B2 | 3/2015 | Nykjaer et al. |
| 9,605,073 B2 | 3/2017 | Nykjaer et al. |
| 2012/0322060 A1 | 12/2012 | Mazella et al. |
| 2017/0072013 A1 | 3/2017 | Gaudriault et al. |
| 2017/0158766 A1 | 6/2017 | Nykjaer et al. |

FOREIGN PATENT DOCUMENTS

| WO | 2004/056385 A2 | 7/2004 |
| WO | 2009/103898 A1 | 8/2009 |
| WO | 2015/110915 A2 | 7/2015 |

OTHER PUBLICATIONS

Diamandis et al, The Biotin-(Strept)Avidin System: Principles and Applicationsin Biotechnology, CLIN. CHEM., 1991, 37, pp. 625-636.*
Peptide Modification, from GenScript, Sep. 14, 2015, pp. 1-3.*
Nestler et al., "Neurobiology of Depression", Neuron, 2002, pp. 13-25, vol. 34, No. 1.
Perlis et al., "Phamnacogenetic Analysis of Genes Implicated in Rodent Models of Antidepressant Response: Association of TREK1 and Treatment Resistance in the STAR*D Study", Neuropsychopharmacology, 2008, pp. 2810-2819, vol. 33, No. 12.
Devader et al., "In vitro and in vivo regulation of synaptogenesis by the novel antidepressant spadin", British Journal of Pharmacology, 2015, pp. 2604-2617, vol. 172, No. 10.
Alloui et al., "TREK-1, a K+ channel involved in polymodal pain perception", The EMBO Journal, 2006, pp. 2368-2376, vol. 25, No. 11.

(Continued)

*Primary Examiner* — Li N Komatsu
(74) *Attorney, Agent, or Firm* — Nixon & Vanderhye (57) ABSTRACT Disclosed are new peptides derived from the neurotensin receptor 3 (NTSR3), and to their use, particularly in the treatment of various diseases, especially depression.

4 Claims, 4 Drawing Sheets
Specification includes a Sequence Listing.

(56) References Cited

OTHER PUBLICATIONS

Krieger et al., "Affinity Purification of Synthetic Peptides", Proceedings of the National Academy of Sciences of the United States of America., 1976, pp. 3160-3164, vol. 73, No. 9.

Moha Ou Maati et al., "A Human TREK-1/HEK Cell Line: A Highly Efficient Screening Tool for Drug Development in Neurological Diseases", PLoS One, 2011, Article e25602, vol. 6, No. 10.

Hivelin et al., "Potentiation of Calcium Influx and Insulin Secretion in Pancreatic Beta Cell by the Specific TREK-1 Blocker Spadin", Journal of Diabetes Research, 2016, Article 3142175, vol. 2016.

International Search Report, dated Mar. 1, 2018, from corresponding PCT application No. PCT/FR2017/052788.

Devader et al., "Serum sortilin-derived propeptides concentrations are decreased in major depressive disorder patients". Journal of Affective Disorders, 2017, pp. 443-447, vol. 2018.

Fist, Licencing Opportunities CNRS patent portfolio related to Central Nervous Systems Disorders, 2014, <http://www.fist.fr/wp-content/uploads/file/Portefeuilles/CNRS>, XP055191985.

\* cited by examiner

PEPTIDES DERIVED FROM THE PROPEPTIDE NTSR3 AND THEIR USE IN THE TREATMENT OF DEPRESSION

CROSS-REFERENCE TO RELATED APPLICATIONS

This application is the national stage of PCT/FR2017/052788 filed Oct. 11, 2017, and claims priority to France application No. 1659781 filed on Oct. 11, 2016, France application No. 1752162 filed on Mar. 16, 2017, and France application No. 1754127 filed on May 11, 2017.

TECHNICAL FIELD OF THE INVENTION

The present invention relates to short peptides derived from the neurotensin receptor 3 (NTSR3) and to their use in various pathologies (diabetes, cancer, epilepsy, stroke, neurodegenerative pathologies, etc.), notably in the treatment of psychiatric pathologies, especially patients suffering from, or having suffered from, depression, for example after a stroke. The present invention relates, in particular, to the use of these peptides for the manufacture of a medicament, for example an antidepressant.

The present invention finds application in the sectors of the pharmaceutical industry and, in particular, in the fields of development of medicaments used in the treatment of various pathologies (diabetes, cancer, stroke, epilepsy, psychiatric diseases, neurodegenerative pathologies, etc.).

In the description below, references in brackets ([ ]) refer to the list of references displayed at the end of the text.

PRIOR ART

Depression is a major public health problem. The most recent works have confirmed the high prevalence of depression: over their whole lifetime, 20% of women and 10% of men have had, are having, or will have a depressive episode [1]. Such figures are obviously striking; they are even more so when we look at the major complication of depression, suicide, which amounts to 12000 deaths per year in countries like France [2].

Depression is a very common and often debilitating disease. It can affect up to 20% of the population in industrialized countries. Its origins are diverse and multiple. This pathology affects the psyche as well as the behavior and physiology of the patients. The treatments for depression are also multiple and the mechanisms of action of the drugs used are not clearly established.

The World Health Organization (WHO) predicts that unipolar depression will be the second leading cause of disability by 2020. To the personal and family suffering of depression is added the important social weight of this pathology. Depression is already one of the leading causes of work stoppage, with an economic burden of more than 30 billion Euros per year. Despite the therapeutic arsenal available to the medical profession, particularly SSRI (Selective Serotonin Reuptake Inhibitors) and SNRI (Serotonin Noradrenaline Reuptake Inhibitors), 30% of the depressed population receives no treatment. In addition, the time of action of antidepressants is of the order of 3 to 6 weeks and side effects are often significant.

In general, it is estimated that 15% of depressed patients die by suicide. In most patients, depression is due to the interaction between a genetic predisposition and environmental factors such as stress or emotional trauma [3]. The disease is common and the antidepressant (AD) market is huge (at least €10 billion a year).

Nevertheless, while these antidepressants improve the state of the patients in approximately 70% of the cases, they bring about a complete remission of the disease only in 30 to 40% of the patients. In addition, nearly one-third of the treated subjects are resistant to existing treatments. This state of affairs makes it all the more necessary to consider new treatments that can take into account the mechanisms of depression [3].

In the therapeutic arsenal made available to the medical profession, tricyclic antidepressants (TCA) with amitriptyline and imipramine were first discovered, followed by monoamine oxidase inhibitors (MAOI), irreversible and non-selective such as phenelzine and pargyline. The adverse effects, in particular the cardiotoxicity of TCA (especially in the case of overdose) and the hypertensive crises of the MAOI (interactions with the alimentary tyramine, the famous "cheese effect") have pushed research towards new molecules of identical therapeutic effectiveness but with better acceptability.

The concept of selectivity then appeared with the inhibitors specific of the reuptake of noradrenaline (NA) or serotonin (5-hydroxytryptamine or 5HT). Phase III clinical trials have demonstrated that these new molecules offer equivalent effectiveness to first-generation antidepressants and better safety, especially in the event of overdose.

Specific serotonin reuptake inhibitors (SSRI) and specific noradrenaline reuptake inhibitors (SNRI) are currently the most widely used molecules [4-5]. AD are thus most often associated with facilitating the transmission of monoaminergic systems.

Although serotonin, noradrenaline and dopamine are definitely implicated, it is now accepted that changes in monoamine levels produced by AD and the adaptive processes that result from them, in particular the alteration of the sensitivity of some of their receptors, cannot explain by themselves the mechanism of action of antidepressants.

Thus, it is difficult to correlate the time of 3 to 6 weeks required to obtain AD with the increase in synaptic levels of monoamines, which occurs as soon as the first administration of the product. In almost half a century, the number of hypotheses about the pathogenesis of depression and its treatment has continued to evolve.

For example, high concentrations of glucocorticoids are generally associated with a negative mood effect, as well as structural alterations of the hippocampus through a decrease in BDNF (Brain-Derivated Neurotrophic Factor) synthesis, excessive secretion of glutamic acid and/or decreased glucose uptake [6].

According to these observations, glucocorticoid synthesis inhibitors and glucocorticoid receptors antagonists exert AD-like effects [7].

Antagonists acting on substance P receptors, particularly NK1, or the CRF receptor (Corticotropin-Releasing Factor), as well as NMDA receptor antagonists, have been developed with some success [8-10].

Various recent studies carried out in stressful situations and models of depression have implicated neurogenesis in the etiology of major depressive disorders [11-13]. It has been shown that all chronic AD treatments, including electroshock, stimulate the proliferation of progenitor cells at the origin of the neurons of the granular layer of the hippocampus.

It is also known that AD modulate the expression of various factors involved in cell survival and growth, such as CREB, Bcl2, or MAP kinases. However, the functional importance of these neoformed neurons in the pathophysiology of mood disorders remains controversial [14].

All these indications demonstrate that depression is a complex disease whose pathophysiology is multifactorial and, consequently, the treatment of such a pathology remains a challenge.

For more than forty years, research on depression and the development of effective drugs has been dominated by the monoaminergic hypothesis. Although monoaminergic neurotransmitters (serotonin, noradrenaline and dopamine) are indisputably implicated, the number of hypotheses about the pathophysiology of depression and the mechanisms of action of AD has continued to evolve.

AD drugs used today produce a range of side effects, including dry mouth, blurred vision, and impaired bowel function (diarrhea or constipation). Although many side effects are transient (such as nausea), some appear to be consistent over time (such as sexual effects) and may affect long-term treatment adherence. This is why the search for new molecules acting on receptors or channels newly identified in depression, is crucial.

Some proteins, receptors and channels, have been implicated in the molecular mechanisms of depression. This is particularly the case of the neurotensin receptor 3 (NTSR3), also called sortilin, whose inactivation in mice produces a phenotype of depression resistance, similar to that observed in mice invalidated for the basal potassium channel TREK-1.

The recent STAR*D (Sequenced Treatment Alternatives to Relieve Depression) study [15] has pharmacogenically identified TREK-1 as the gene involved in the antidepressant response in humans. This study also suggests the usefulness of an animal model for the search for antidepressant treatments in the identification of candidate genes for a study in humans. TREK-1 channel blockers therefore represent a new concept in the field of antidepressant drug design.

To date, a molecule effectively interacting with TREK-1 channels has been identified. It is a peptide of 44 amino acids, called propeptide (PE): QDRLDAPPPPAAPL-PRWSGPIGVSWGLRAAAAGGAFPRGGRWRR (SEQ ID NO: 1) released during the maturation by the furin of neurotensin receptor 3 (NTSR3) which becomes a ligand of this same receptor. Interestingly, it has been shown that this propeptide is also able to block the activity of the TREK-1 channel. It has been shown that a portion of 17 amino acids derived from said propeptide, called spadin (YAPLPRWSG-PIGVSWGLR, SEQ ID NO: 2), carries all the binding activity on the receptor [16]. It has recently been shown that spadin specifically blocks TREK-1 channels. It behaves as an antidepressant in rodent models of depression, without causing side effects on other functions of this channel and other potassium channels at the cardiac and glycemic index levels [17]. Recently, the role of spadin has been identified in the regulation of synaptogenesis [18].

There is therefore a real need for new molecules that may be used for the treatment of depression, molecules that are more effective, better tolerated and have faster action.

DESCRIPTION OF THE INVENTION

The present invention has precisely the role of responding to the need and solving the disadvantages of the prior art.

For this purpose, the inventors have investigated whether smaller peptides resulting from the degradation of spadin could also have an antidepressant role, and have unexpectedly identified new active peptides derived from the propeptide (PE), modified or ont, in particular peptide PE(13-27) of sequence SEQ ID NO: 4 (PLPRWSGPIGVSWGL) and peptide PE(14-25) of sequence SEQ ID NO: 5 (LPRWSGPIGVSW) which correspond to degradation products of spadin, and retain the properties of antidepressants.

In addition, the PE(22-28) peptide of sequence SEQ ID NO: 3 (GVSWGLR) also derived from the propeptide was used as a base peptide for the design of other peptides: biotinylated peptide PE(22-28), peptide PI-PE(22-28) of sequence SEQ ID NO: 6 (PIGVSWGLR), biotinylated peptide PI-PE(22-28), peptide G/A-PE(22-28) of sequence SEQ ID NO: 7 (AVSWGLR) corresponding to the sequence SEQ ID NO: 3 in which the glycine at position 22 was replaced by an alanine, the biotinylated G/A-PE(22-28) peptide, the dansyl PE(22-28) peptide corresponding to the sequence SEQ ID NO: 3 in which a dansyl chemical group was added at the N-terminal, the O-methyl-PE(22-28) and O-ethyl-PE(22-28) peptides corresponding to the sequence SEQ ID NO: 3 in which an O-methyl or O-ethyl chemical group was respectively added at the C-terminal.

These PE(22-28) analogs, hereinafter referred to as spadin analogs, exhibit significant antidepressant (AD) action in mice, as measured by behavioral tests (forced swimming test, learned helplessness test), and rapidly and more efficiently induce neurogenesis and synaptogenesis. Because the physiological targets of these spadin analogs are the same as those of spadin, their mechanisms of action are very similar to those of spadin. These analogs of spadin act by the inhibition of the TREK-1 channel with a better affinity (×333) than spadin itself (0.12 nM for the spadin analogs vs 40 nM for spadin). Given the better affinity and the smaller size of the spadin analogs, the main advantages of these peptides are firstly a decrease in the amount of product to be administered resulting in a decrease in the potentially associated side effects (toxicity, tumorigenicity, etc. . . . ), and secondly a decrease in the cost of production as well as its availability for any known route of administration (icy, iv, ip and oral). It has been previously shown that spadin has a rapid effect, 4 days instead of 21 days for conventional antidepressants. Thus the use of short peptides that are both quickly available and rapidly removed from the organism represents a guarantee of an effective therapeutic product without side effects; which is of crucial importance in public health.

The object of the present invention is therefore a peptide derived from the propeptide (PE) of the neurotensin receptor 3 (NTSR3) selected from the peptide PE(13-27) of sequence SEQ ID NO: 4 (PLPRWSGPIGVSWGL), the peptide PE(14-25) of sequence SEQ ID NO: 5 (LPRWSGPIGVSW), the biotinylated peptide PE(22-28) corresponding to the sequence SEQ ID NO: 3 biotinylated, the peptide PI-PE(22-28) of sequence SEQ ID NO: 6 (PIGVSWGLR), the biotinylated peptide PI-PE(22-28) corresponding to the sequence SEQ ID NO: 6 biotinylated, the peptide G/A-PE(22-28) of sequence SEQ ID NO: 7 (AVSWGLR) corresponding to the sequence SEQ ID NO: 3 in which the glycine at position 22 has been replaced by an alanine, the biotinylated peptide G/A-PE(22-28) corresponding to the sequence SEQ ID NO: 7 biotinylated, the dansyl-PE(22-28) peptide corresponding to the sequence SEQ ID NO: 3 in which a dansyl chemical group was added at the N-terminal, and the peptides O-methyl-PE(22-28) and O-ethyl-PE(22-28) corresponding to the sequence SEQ ID NO: 3 in which an O-methyl or O-ethyl chemical group was added at the C-terminal, respectively.

The present invention also relates to a nucleic acid sequence encoding a peptide of the invention. This sequence is preferably usable for manufacturing the peptide of the present invention or a fragment or derivative thereof by transfection. This is, for example, the sequence with the GenBank accession numbers for the messenger RNAs of sortilin SORT 1, in the mouse: NM_019972, in humans: NM_002959.

The present invention also relates to a vector comprising a nucleic acid sequence according to the invention. It may be any suitable vector for the transformation of a host cell for the purpose of manufacturing a peptide of the present invention by said cell through a genetic recombination technique. The vector may be obtained from a vector chosen, for example, from the group comprising pIRES and pIRES2 and their derivatives, pcDNA3 and its derivatives, pGEX and its derivatives.

The present invention also relates to a host cell comprising a peptide according to the present invention and/or a nucleic acid sequence according to the present invention and/or a vector according to the present invention. The host cell may be any cell suitable to be transformed and to manufacture said peptide of the invention or fragment or derivative thereof. It may be, for example, COS-7, HEK 293 and derived, N1 E115 and related cells.

The present invention thus also relates to a method for producing a peptide according to the invention comprising the following steps:
 transfecting a host cell with a nucleic acid according to the invention or transforming a host cell with a vector of the invention;
 cultivating said host cell under conditions enabling the expression of a peptide according to the invention, and recovering said peptide.

The transfection and transformation techniques that may be used to manufacture a peptide of the present invention are those known to those skilled in the art, for example those described in Alloui A. et al., EMBO J. 2006 [19].

According to the invention, given the small size of the peptides of the invention, the preferred method of production of the peptide is chemical synthesis, for example in the solid phase. Any technique known to those skilled in the art may be used. For example, the peptide may be synthesized according to the solid phase technique of Krieger D. E. et al, Proc Nat Acad Sci U.S.A. 1976 [20].

The peptides of the invention open a new way in the establishment of a new class of antidepressants and new therapeutic strategies for depression.

The object of the present invention is also a peptide according to the invention for use as a medicament, in particular as an antidepressant.

The object of the present invention is also a peptide according to the invention for use in the treatment of various pathologies such as diabetes, cancer, stroke, neurodegenerative pathologies, psychiatric pathologies, in particular depression, for example post-stroke depression. These hypotheses are supported by several experimental facts. TREK-1 channels are present on the surface of beta-pancreatic cells such as beta-TC3 cells. In addition, spadin (YAPLPRWSGPIGVSWGLR, SEQ ID NO: 2) has been shown to increase insulin secretion further to hyperglycemia (Hivelin C. et al., J Diabetes Res. 2016) [27]. In addition, on the ßTC3 cells, the inventors have demonstrated that the peptide PE(22-28) of sequence SEQ ID NO: 3: GVSWGLR blocks arachidonic acid (aa) sensitive potassium currents. Insofar as spadin, peptide PE(22-28), and the peptides of the present invention have the same physiological targets, these peptides may also be considered as hypoglycemic molecules. Furthermore, TREK-1 channels are also present on the surface of cancer cells such as LNCaP cells (prostate cancer). On the LNCaP cells, the inventors have demonstrated that the PE(22-28) peptide blocks arachidonic acid (aa) sensitive potassium currents and inhibits their growth. The peptide PE(22-28) and the peptides of the present invention have the same physiological targets, and thus, they may also be considered to have anticancer activity. The use of a peptide according to the invention can also be envisaged in neuroprotection against stroke, or epilepsy.

The peptides of the present invention as defined above, with the exception of G/A-PE(22-28), are natural products which constitute a new type of antidepressant. They enable avoiding all undesirable side effects of drugs currently used for the treatment of depression. The side effects of the drugs used in the prior art come from their chemical nature. These prior art drugs are molecules that often have the property of passing through cell membranes passively, resulting in non-specific interactions with intracellular effectors. The peptide nature of the present invention enables avoiding this problem.

Furthermore, the direct action of a peptide of the present invention on the potassium channel TREK-1 could well reduce the time of action, often long, of a conventional antidepressant.

Other advantages may appear to those skilled in the art upon reading the examples which follow, given of course by way of illustration and non-limiting with reference to the appended figures.

EXAMPLES

Example 1: Action of Spadin Analogs on Trek-1 Canal Activity

All experiments measuring the effect of spadin analogs and spadin were performed on ßTC3 or LNCaP or HEK293 cells stably transfected with the TREK-1 channel, hTREK-1/HEK293. The hTREK-1/HEK293 cell line was prepared in the laboratory [21]. These cells also express a reporter gene: E-Green Fluorescent Protein (EGFP) enabling their visualization.

These cells were seeded at a density of 20,000 cells/dish of 35 mm diameter, 24 to 72 hours before being used.

The HEK293 cells were cultured in DMEM medium (Gibco)/10% fetal calf serum (FCS, ICN)/1% streptomycin+penicillin mixture (Gibco)/1% glutamax (Gibco)/0.5 mg/mL of G418 (Sigma) at 37° C. in the presence of 5% $CO_2$.

The ßTC3 cells were cultured in RPMI 1640 medium supplemented with 2.5% FCS, 50 µM beta-mercaptoethanol, 10 mM HEPES, 1 mM sodium pyruvate, 50 µg/ml gentamycin and 1% of a streptomycin+penicillin mixture, at 37° C. in the presence of 5% $CO_2$.

The LNCaP cells were cultured in DMEM medium (Gibco)/10% fetal calf serum (FCS, ICN)/1% streptomycin+penicillin mixture (Gibco)/1% glutamax (Gibco)/at 37° C. in the presence of 5% $CO_2$. At day 1, the hTREK-1/HEK293 or BTC3 or LNCaP cells were seeded at 20,000 cells per 35 mm diameter dish containing 2 ml of culture medium. From day 2 to day 4, the cells were measured by electrophysiological methods.

All measurements were made at room temperature, i.e. at 21-22° C. The hTREK-1/HEK293 cells were identified by the fluorescence emitted by EGFP after excitation at 480 nm.

The whole-cell patch clamp technique was used to measure TREK-1 channel activity. The equipment used is the RK 400 patch-clamp amplifier (Axon Instruments, U.S.A.). The 1.3 to 8 MΩ resistance patch pipettes were prepared from borosilicate glass capillaries and were filled with solution 155 mM KCl, 3 mM $MgCl_2$, 5 mM EGTA, 10 mM HEPES/KOH pH 7.2.

The cell culture medium was replaced with a solution 150 mM NaCl, 5 mM KCl, 3 mM $MgCl_2$, 1 mM $CaCl_2$, 10 mM HEPES/NaOH pH 7.4 containing 10 mM tetraethylammonium chloride, 3 mM 4-aminopyridine. The cells were continuously infused with this solution. The resting potential of the membrane of the measured cell was set at −80 mV.

The voltage variations were obtained either by continuous ramp (from −100 to +60 mV) or by a potential jump of 10 mV (from −100 to +60 mV, 1.5 seconds per jump). The data obtained were analyzed with the Pclamp software.

Figure 1:
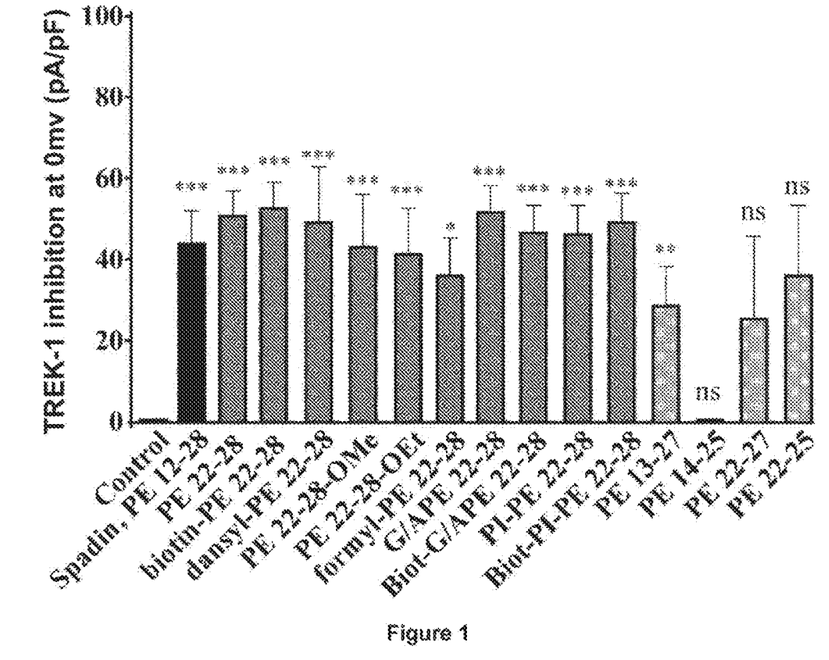
FIG. 1 shows the action of the spadin analogs of the invention on the activity of the TREK-1 channel, in comparison with that of spadin and peptide PE(22-28), measured in vitro by electrophysiological experiments.
Figure 2:
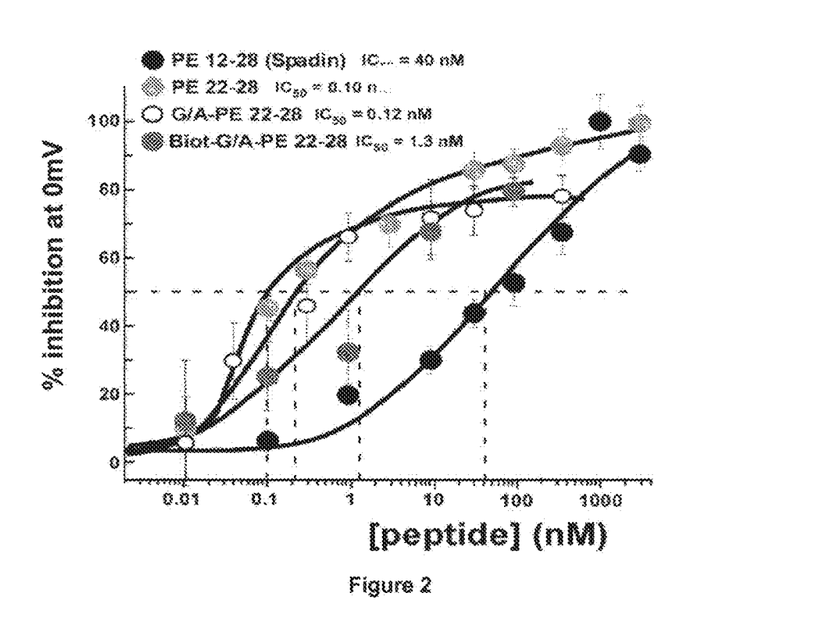
FIG. 2 shows the action of the spadin analogs G/A-PE (22-28) and biotinylated G/A-PE(22-28) on the activity of the TREK-1 channel, in comparison with that of spadin and peptide PE(22-28), measured in vitro by electrophysiological experiments.

The currents described in FIGS. 1 and 2 were obtained at 0 mV. The results of FIGS. 1 and 2 expressed are the averages±standard deviation. The $IC_{50}$ value of FIG. 2 was obtained by plotting the experimental data using a sigmoidal function.

The channel activity was then measured by the "patch-clamp" technique in whole cell configuration as described above.

The inhibitions of TREK-1 channel activity measured at 0 mV of all the spadin analogs of the invention and spadin are shown in FIG. 1. It indicates that all spadin analogs, except peptides PE(14-25), PE(22-25) and PE(22-27), are able to block the activity of TREK-1 channels to the same extent as spadin (PE(12-28)).

A dose-response curve of TREK-1 channel activity inhibition measured at 0 mV was performed in the presence of the analogs G/A-PE(22-28) or biotinylated G/A-PE(22-28) or spadin. These curves are shown in FIG. 2. It indicates a half-effect concentration ($IC_{50}$) of 0.12 nM and 0.13 nM for peptides G/A-PE(22-28) and biotinylated G/A-PE(22-28), respectively, and 40 nM for spadin.

All of the results show that most spadin analogs are able to block TREK-1 channels with better affinity (×333) than spadin and, for some analogs, with an affinity equivalent to that of peptide PE(22-28).

Figure 7:
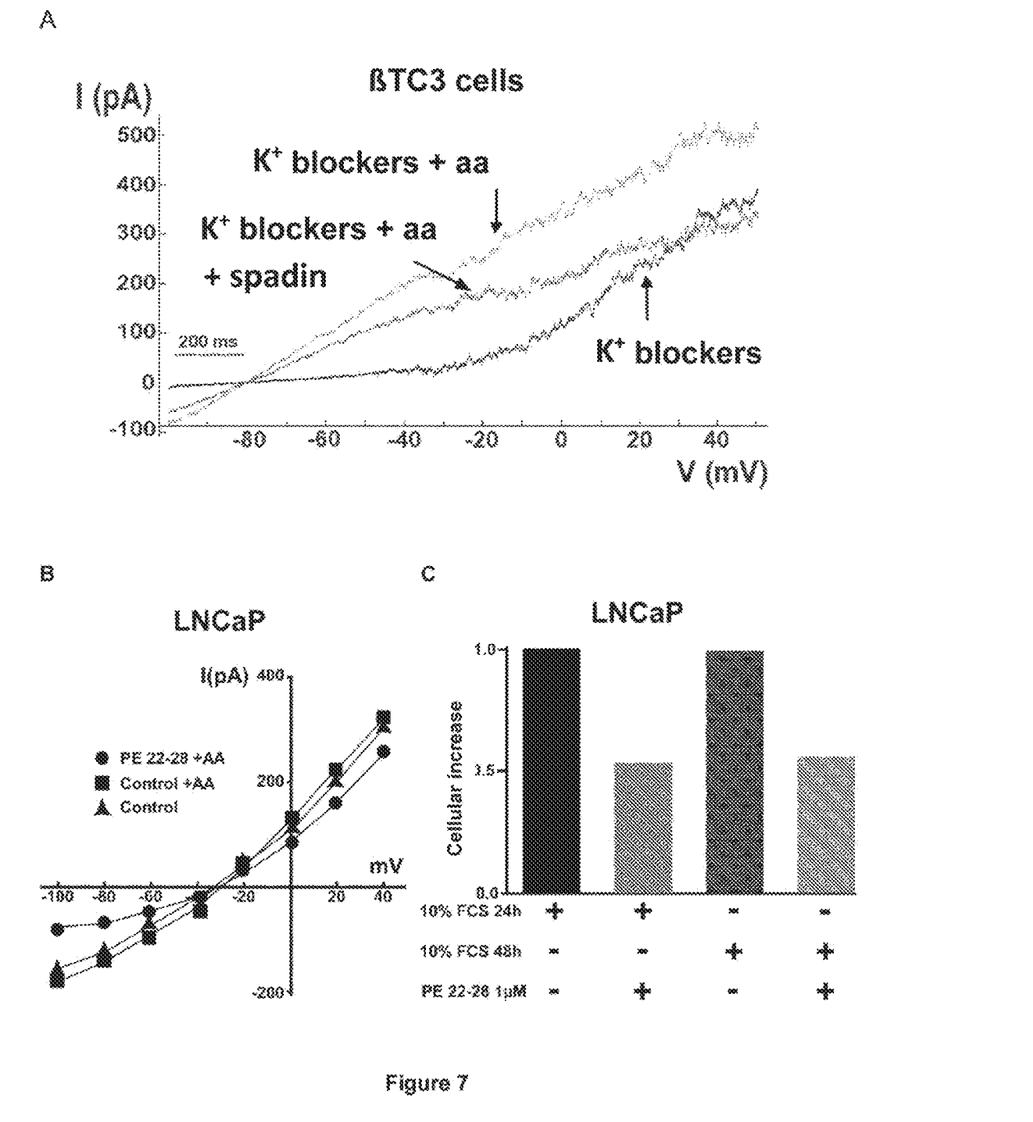
FIG. 7 shows the action of the peptide PE(22-28) on the activity of the TREK-1 channel expressed in the pancreatic cells ßTC3 (A) and cancerous cells LNCaP (B), measured in vitro by electrophysiological experiments, as well as on the growth of LNCaP cancer cells (C).

The current intensities measured as a function of the voltage [I=f(V)] applied on the ßTC3 cells described in FIG. 7A, indicate that the spadin is capable of blocking the TREK-1 channels expressed on the ßTC3 cells and previously activated with arachidonic acid (aa). The spadin and the peptides of the present invention have the same physiological targets, thus these peptides may be considered as hypoglycemic molecules.

The current intensities measured as a function of the voltage [I=f(V)] applied to the LNCaP cells described in FIG. 7B, indicate that the peptide PE(22-28) is capable of blocking the TREK-1 channels expressed on the LNCaP cells and previously activated with arachidonic acid (aa). In addition, the growth of LNCaP cells obtained after counting the cells in culture after 24 or 48 h, in the presence or absence of the peptide PE(22-28), indicates that the peptide PE(22-28) is capable of inhibiting the cell growth. The peptide PE(22-28) and the peptides of the present invention have the same physiological targets, thus these peptides may also be considered as having anti-cancer activity.

Example 2: Behavior Tests

Forced Swimming Test (FST)

A classical behavioral test was developed to determine the antidepressant activity of a substance (Nestier E. J. et al, 2002, Cryan J. and Holmes A., 2005) [22, 23]. The effects of the spadin analogs of the present invention were compared to those of the saline solution in which the spadin analogs of the invention were dissolved and those of the spadin. The mouse strain used was strain C57Bl/6J.

Saline solution, spadin analogs and spadin were administered to the mice intraperitoneally (IP) at a dose of 100 µg/kg in a bolus of 100 µl.

The experiment consisted in immersing the mouse for 6 minutes in a container of 15 cm in diameter, 30 cm high containing 11 cm of water at 22° C., 30 minutes after administration of the substance to be tested, and measuring the time of immobility during the last 4 minutes.

Figure 3:
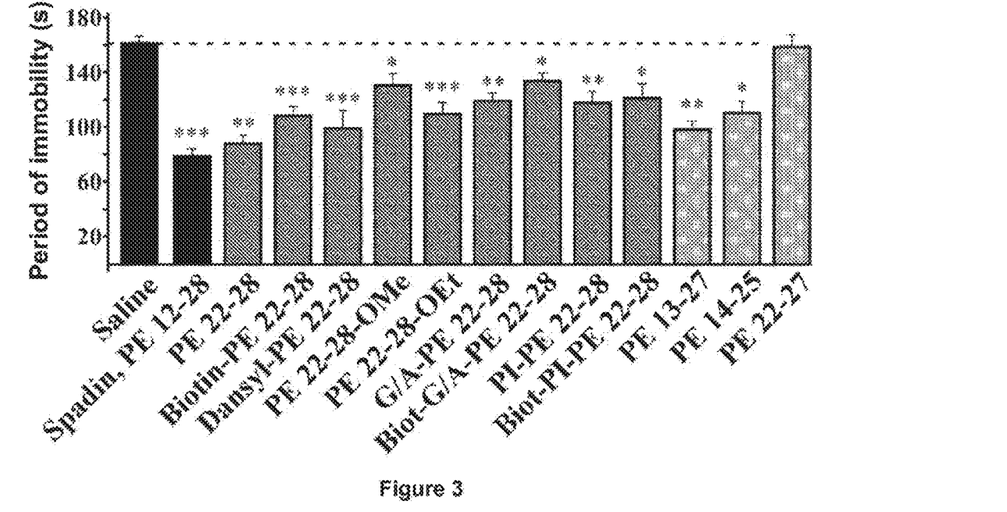
FIG. 3 shows the antidepressant activity of the spadin analogs according to the present invention, in comparison with that of spadin and peptide PE(22-28), measured in vivo in mice subjected to the forced swimming test (FST).

The results of these tests are shown in FIG. 3: FST tests, the values±SEM were statistically compared with the control condition (physiological saline) *** $p<0.001$, ("ANOVA" test=test of analysis of variances).

The results show that spadin analogs capable of inhibiting the action of TREK-1 channels are effective in the forced swimming test after their IP injection in mice. On the other hand, the peptide PE(22-27) that is not effective in inhibiting TREK-1 channels is also ineffective in reducing the time of immobility in the forced swimming test.

Learned Helplessness Test (LHT)

Learned resignation or learned helplessness is a model based on the repeated administration of electric shocks to induce a resigned state in the animal. Indeed, it has been shown that animals receiving unavoidable electric shocks resign themselves to receiving them and do not try to flee (Seligman and Beagley, Learned Helplessness in the Rat J Comp Physiol Psychol 88, 534-541, 1975) [24].

The apparatus comprises two compartments separated by a sliding door and with a floor consisting of a metal grid through which the electrical pulses are administered. The learned helplessness protocol is divided into two stages, an animal conditioning stage and a test stage.

The conditioning was carried out over a period of four days during which time the mice received 360 non-avoidable electric shocks of 0.3 mA for one hour (the door, separating the two compartments, being closed). The shocks lasted for 2 seconds and an interval of 8 seconds was respected between each shock. This conditioning step leads to a phenomenon of helplessness in animals.

On the day of the test, the mice were placed in the same compartments but with a possibility of escaping the shock. The test counted 30 trials. During the administration of the shock, the door separating the two compartments opened, allowing the animals to flee. When the animal changes compartment the test is finished and the shock stops. If the mouse does not change compartment the shock stops after 24 seconds and the test ends. This test made it possible to record the escape latencies of the animals. The thirty tests were then grouped by 5 and the average escape time was calculated.

The molecules, G/A-PE(22-28) and biotinylated G/A-PE (22-28) or saline solution are injected 30 minutes before the conditioning in the form of a bolus of 100 µL of a $10^{-6}$M solution prepared in saline solution.

Figure 4:
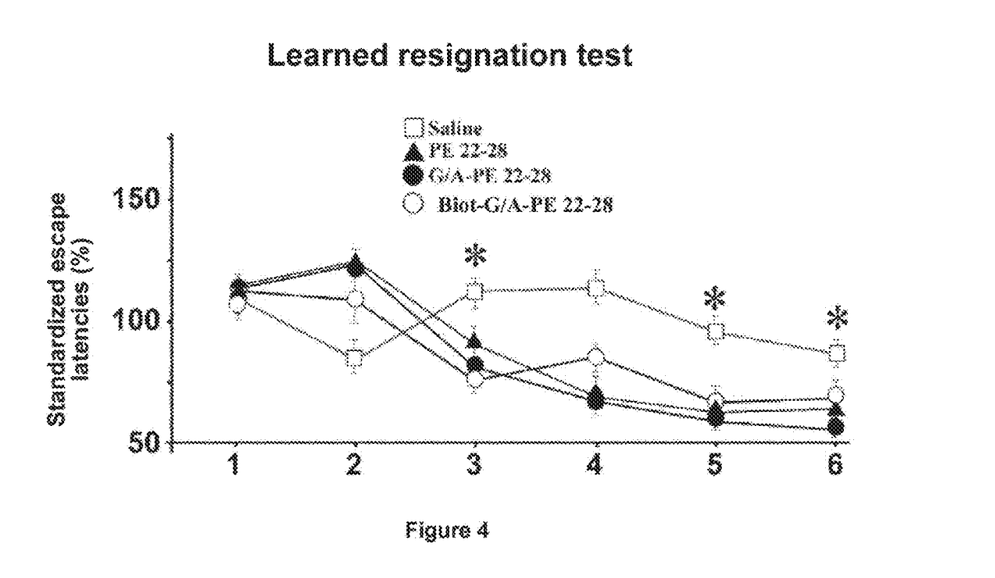
FIG. 4 shows the antidepressant activity of the spadin analogs G/A-PE(22-28) and biotinylated G/A-PE(22-28), in comparison with that of spadin and peptide PE(22-28), measured in vivo in mice subjected to the learned helplessness test (LHT).

The results presented in FIG. 4 show that peptides G/A-PE(22-28) and biotinylated G/A-PE(22-28) administered to mice under the same conditions as previously described, are capable of reducing the escape latencies in the resignation test learned in an equivalent manner to peptide PE(22-28).

Example 3: Action of Spadine Analogs on Neurogenesis and Synaptogenesis

Study of Neurogenesis by Immunohistochemistry

BrdU (5-bromo-2'-deoxyuridine) is a synthetic nucleoside analogous to thymidine. It is incorporated during DNA replication during phase S (chromosome duplication during interphase) of the cells in division. Injection of BrdU makes it possible to visualize the cells in division of the tissue to be analyzed by means of immunological labeling. In the present study, the hippocampal neurogenesis of the mice was evaluated after treatment with spadin or the different analogs.

After the behavioral tests, the mice were injected with BrdU at a final concentration of 120 mg/kg intraperitoneally, according to the modified protocol of Beauquis, J. et al. (Eur J Neurosci 23, 1539-1546, 2007) [25]. Four injections of 300 µl at 10 mg/ml, spaced two hours apart, were performed. 24 hours after the injections, the mice were anesthetized with pentobarbital (100 mg/kg) and then perfused intracardially. During the intracardiac perfusion, physiological saline was administered to remove all blood from the body of the mice, and then 4% paraformaldehyde (PFA) was perfused to fix the organs. Post-fixation in 4% PFA was also performed overnight. The brains of the mice were cut with a vibratome (Leica), which allowed 40 µm floating frontal sections to be obtained. The sections selected for the immunological reaction were those ranging from bregma 3.3 to 5.3. Eight sections were selected with a regular spacing, allowing the entire hippocampus to be covered while remaining homogeneous from one brain to another.

The immunological reaction was performed by incubating an anti-BrdU primary antibody (BD Pharmingen, 1/8000), with the brain sections, overnight at 4° C. The brain sections were then washed in PBS (Phosphate Buffered Saline) and incubated for two hours with the secondary antibody (biotinylated goat anti-mouse antibody, Vector laboratories, 1/400). A one-hour incubation in an avidine/biotin/peroxidase complex (ABC Vectastain Kit, Vector Laboratories) was carried out in order to amplify the immunological reaction. Finally, the revelation was made using a peroxidase substrate kit (Vector Laboratories) containing a solution of nickel, a solution of 3-3'diaminobenzidine and $H_2O_2$.

The sections were then mounted on slides and fixed with Entellan. BrdU-positive cells of the dentate gyrus of the hippocampus were counted in both hemispheres of each brain. The number of cells obtained on the 8 sections was then multiplied by 40 to account for the total number of proliferating cells throughout the hippocampus.

Figure 5:
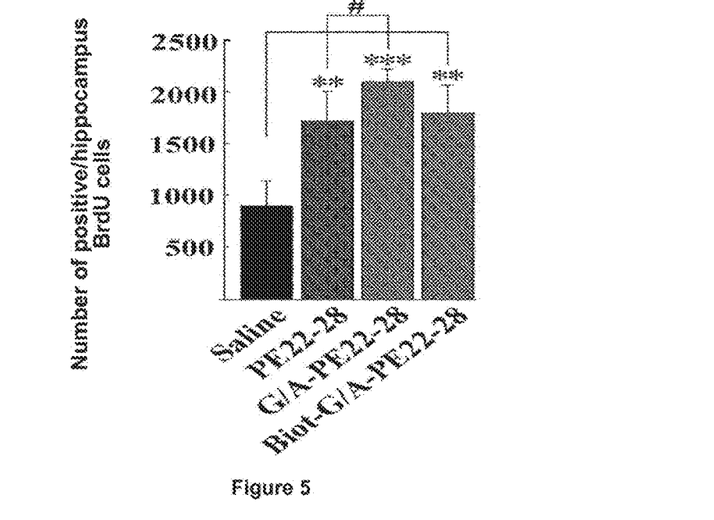
FIG. 5 shows the immunohistochemical study of the action of the spadin analogs G/A-PE(22-28) and biotinylated G/A-PE(22-28) in comparison with that of the peptide PE(22-28), on neurogenesis.

The results shown in FIG. 5 show that the peptides G/APE(22-28) and biotinylated G/A-PE(22-28) are capable of inducing an increase in neurogenesis after only four days of treatment. These increases are greater than the increase obtained under the same conditions for the unmodified peptide PE(22-28).

Synaptogenesis

Pregnant female C57Bl/6J mice (20-25 g, Janvier Labs, St Berthevin, France) were anesthetized by inhalation of 2% isoflurane mixed with 30% oxygen and 70% nitrous oxide, and then sacrificed. The embryos (E14) were removed and the cerebral cortex was dissected in PBS containing 1% glucose. Neurons were prepared from cerebral cortex by mechanical dissociation, as described in Brewer and Torricelli, 2007 [26]. The dissociated neurons were distributed in poly-L-lysine treated plates and cultured for up to 10 days in neurobasal medium containing 2% B27 (Invitrogen, Fisher Scientific, Illkirch, France) and 50 µg/ml gentamycin (Sigma France), at 37° C. under 5% $CO_2$.

Analogs of spadin G/A-PE(22-28) and biotinylated G/A-PE(22-28) were synthesized by Covalab, Villeurbanne, France.

The cortical neuron cultures, isolated from neocortex of C57B16/J mouse embryos (Janvier) at the 14-day stage (E14), were incubated with 1 µM of each spadin analog. Incubations were performed in Earle's-Tris-HEPES buffer, pH 7.4, containing 140 mM NaCl, 5 mM KCl, 1.8 mM $CaCl_2$, 3.6 mM $MgCl_2$, and 0.1% of BSA.

Cortical neurons treated with peptides G/A-PE(22-28) and biotinylated G/A-PE(22-28) for different durations (0, 5, 8, 24 and 36 hours) were homogenized in Laemmli buffer and analyzed using 10% SDS-Page gels. The separated proteins were then transferred from the gels onto nitrocellulose membranes (VWR, Fontenay-sous-Bois, France) and blocked either with 5% skim milk or with 5% BSA in PBS, for 30 minutes at room temperature. The membranes were incubated with antibodies directed against the PSD-95 protein (Cell Signaling, unlabeled, Montigny-le-Bretonneux, France), overnight, at 4° C. The ß-actin contents were determined after extraction using a 1/5000 dilution of anti-β-actin antibodies (Santa Cruz mouse monoclonal antibody, dilution 1/5000). After 4 washes in PBS-Tween 0.1%, HRP-conjugated anti-mouse and anti-rabbit secondary antibodies (Amersham Biosciences, Orsay, France, 1/10000) are incubated for 1 hour at room temperature. The proteins were detected with ECL Plus detection reagents (Amersham Biosciences) using the LAS-3000 imaging system (Fujifilm, Düsseldorf, Germany). The relative intensities of each labeled band were analyzed by densitometric scanning using ImageJ software (Wayne Rasband, National Institute of Health, Bethesda, Md., USA). Protein activation was normalized using total ß-actin as indicated.

Figure 6:
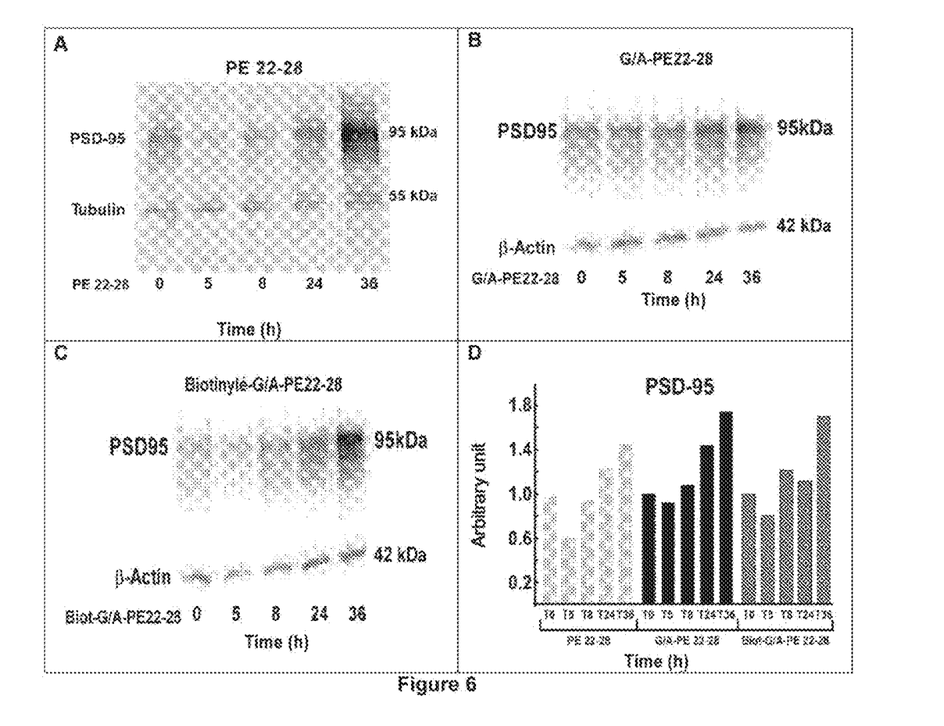
FIG. 6 shows the study of the action of spadin analogs G/A-PE(22-28) and biotinylated G/A-PE(22-28) (B and C, respectively), in comparison with that of the peptide PE(22-28) (A), on synaptogenesis (D) histogram of PSD-95 for each peptide.

The results shown in FIG. 6 show that spadin analogs rapidly increased synaptogenesis. Cortical neurons treated with the spadin analogs G/A-PE(22-28) or biotinylated G/A-PE(22-28) (1 µM) display increased PSD-95 synaptic protein expression observable after 24 hours and more importantly after 36 hours. It should be noted that with the exception of a slight decrease during the first 5 hours, treatments with spadin analogs continuously increase the expression of PSD-95 until 36 h (FIG. 6D). These increases are greater than the increase obtained under the same conditions for the unmodified peptide PE(22-28). These results show that spadin analogs G/A-PE(22-28) or biotinylated G/A-PE(22-28) increase neurogenesis more strongly than peptide PE(22-28) but also synaptogenesis more strongly, indicating that the fate of a majority of neoformed cells is to generate mature neurons.

LIST OF REFERENCES

[1] Wong, M. & Licinic, J. Research and treatment approaches to depression. Nat Rev Neurosci. 2, 343-351 (2001).
[2] Moller H J. Suicide, suicidality and suicide prevention in affective disorders. Acta Psychiatr Scand; 418 (suppl): 73-80 (2003).
[3] Nestler, E. et al. Neurobiology of depression. Neuron 34, 13-25 (2002).
[4] Baghai T C, Volz H P, Moller H J. Drug treatment of depression in the 2000s: An overview of achievements in the last 10 years and future possibilities. World J Biol Psychiatry; 7(4):198-222 (2006).
[5] Weilburg J B. An overview cf SSRI and SNRI therapies fer depression. Manag Care. June; 13 (6 Suppl Depression): 25-337 (2004).
[6] Manji H K, Gottesman I I, Gould T D. Signal transduction and genes-tobehaviors pathways in psychiatric diseases. Sci STKE; 207: pe49 (2003).
[7] Reus V I, Wolkowitz O M. Antiglucocorticoid drugs in the treatment of depression. Expert Opin Investig Drugs; 10: 1789-96 (2001).
[8] Griebel G, Simiand J, Steinberg R, et al. 4-(2-Chloro-4-methoxy-5-methylpheny-N-[(1 S)-2-cyclopropyl-1-(3-fluoro-4-methylphenyl)ethyl]5-methylN-(2-propynyl)-1, 3-thiazol-2-amine hydrochloride (SSR1 25543A), a potent and selective corticotrophin-releasing factor(1) receptor antagonist. II.
Characterization in rodent models of stress-related disorders. J Pharmacol Exp Ther; 301: 333-45 (2002).
[9] Kramer M S, Gutler N, Feighner J, et al. Distinct mechanism for antidepressant activity by blockade of central substance P receptors. Science 281: 1640-1645 (1998).
[10] Skolnick P. Antidepressants for the new millennium. Eur J Pharmacol 375:31-40(1999).
[11] Kempermann G, Kronenberg G. Depressed new neurons. Adult hippocampal neurogenesis and a cellular plasticity hypothesis of major depression. Biol Psychiatry; 54: 499-503 (2003).
[12] Malberg J E, Schecter L E. Increasing hippocampal neurogenesis: a novel mechanism for antidepressant drugs. Curr Pharm Des; 11: 145-155 (2005)
[13] Duman, R. & Monteggia, L. A neurotrophic model for stress-related mood disorders. Biol Psychiatry. (9, 1116-1127 (2006).
[14] Henn F A, Vollmayr B. Neurogenesis and depression: etiology or epiphenomenon? Biol Psychiatry; 56: 146-50. (2004).
[15] Perlis, R. H., Moorjani, P., Fagerness, J., Purcell, S., Trivedi, M. H., Fava, M., Rush, A. J., Smoller, J. W., Pharmacogenetic Analysis of Genes Implicated in Rodent Models of Antidepressant Response: Association of TREK1 and Treatment Resistance in the STAR(*)D Study. Neuropsychopharmacology. November; 33(12): 2810-9 (2008)
[16] Jean Mazella, Olivier Petrault, Marc Borsotto, Catherine Heurteaux, Catherine Widmann Peptide dérivé du récepteur 3 de la neurotensine et utilisation dans le traitement de maladies psychiatriques. WO2009103898 A1; PCT/FR2008/001784, date de publication 27 aoOt 2009
[17] H. Moha ou Maati, J. Veyssiere, F. Labbal, T. Coppola, C. Gandin, C. Widmann, J. Mazella, C. Heurteaux, M. Borsotto. Spadin as a new antidepressant: absence of side effects on TREK-1 controlled functions. Neuropharmacology. 2012 January; 62(1):278-88. doi: 10.1016/j.neuropharm.2011.07.019. Epub 2011 July 22.
[18] C. Devader, A. Khayachi, J. Veyssiere, H. Moha ou Maati, M. Roulot, S. Moreno, M. Borsotto, S Martin, C. Heurteaux and J. Mazella. In vitro and in vivo regulation of synaptogenesis by novel antidepressant spadin. British Journal of Pharmacology. 2015 May; 172(10):2604-17. doi: 10.1111/bph.13083. Epub 2015 Mar. 24.
[19] Alloui A, Zimmermann K, Mamet J, Duprat F, Noël J, Chemin J, Guy N, Blondeau N, Voilley N, Rubat-Coudert C, Borsotto M, Romey G, Heurteaux C, Reeh P, Eschalier A, Lazdunski M. TREK-1, a K+ channel involved in polymodal pain perception. EMBO J. 2006 Jun. 7; 25(11): 2368-76.
[20] Krieger D E, Erickson B W, Merrifield R B. Affinity purification of synthetic peptides. Proc Natl Acad Sci USA. 1976 September; 73(9):3160-4.
[21] Moha ou Maati, H., Peyronnet, R., Devader, C., Veyssiere, J., Labbal, F., Gandin, C., Mazella, J., Heurteaux, C., Borsotto, M. A. human TREK-1/HEK cell une: a highly efficient screening tool for drug development in neurological diseases. PLoS One. 2011; 6(10):e25602. doi: 10.1 371/journal.pone.0025602. Epub 2011 Oct. 14. (2011).
[22] Nestler, E. J. et al. Preclinical models: status of basic research in depression. Biol Psychiatry. 15, 503-528 (2002).
[23] Cryan, J. & Holmes, A. The ascent of mouse: advances in modelling human depression and anxiety. Nat Rev Drug Discov. 4, 775-790 (2005).
[24] Seligman and Beagley, Learned helplessness in the rat. J Camp Physiol Psychol 88, 534-541. (1975).
[25] Beauquis, J. et al. Reduced hippocampal neurogenesis and number of hilar neurones in streptozotocin-induced diabetic mice: reversion by antidepressanttreatment. Eur J Neurosci 23, 1539-1546. (2006)
[26] Brewer et Torricelli J R. Isolation and culture of adult neurons and neurospheres. Nat Protoc.; 2(6):1 490-8. (2007).
[27] Hivelin C, Béraud-Dufour S, Devader C, Abderrahmani A, Moreno S, Moha Ou Maati H, Djillani A, Heurteaux C, Borsotto M, Mazella J, Coppola T.(2016) Potentiation of Calcium Influx and Insulin Secretion in Pancreatic Beta Cell by the Specific TREK-1 Blocker Spadin. J Diabetes Res. 2016:2016:3142175. doi: 10.1155/2016/3142175).

The invention claimed is:

1. A peptide derived from the propeptide (PE) of the neurotensin receptor 3 (NTSR3) selected from the group consisting of: the peptide G/A-PE(22-28) consisting of the amino acid sequence of SEQ ID NO: 7 (AVSWGLR), and the biotinylated peptide G/A-PE(22-28) corresponding to the sequence SEQ ID NO: 7 biotinylated.

2. A medicament comprising the peptide according to claim 1.

3. The medicament according to claim 2, wherein the medicament is an antidepressant.

4. A method for treating depression in a subject in need thereof, said method comprising administering to the subject a therapeutically effective amount of the peptide according to claim 1.

* * * * *

SEQUENCE LISTING

<160> NUMBER OF SEQ ID NOS: 7

<210> SEQ ID NO 1
<211> LENGTH: 44
<212> TYPE: PRT
<213> ORGANISM: Artificial Sequence
<220> FEATURE:
<223> OTHER INFORMATION: Propeptide PE

<400> SEQUENCE: 1

Gln Asp Arg Leu Asp Ala Pro Pro Pro Ala Ala Pro Leu Pro Arg
1               5                   10                  15

Trp Ser Gly Pro Ile Gly Val Ser Trp Gly Leu Arg Ala Ala Ala Ala
            20                  25                  30

Gly Gly Ala Phe Pro Arg Gly Gly Arg Trp Arg Arg
        35                  40

<210> SEQ ID NO 2
<211> LENGTH: 18
<212> TYPE: PRT
<213> ORGANISM: Artificial Sequence
<220> FEATURE:
<223> OTHER INFORMATION: Spadine

<400> SEQUENCE: 2

Tyr Ala Pro Leu Pro Arg Trp Ser Gly Pro Ile Gly Val Ser Trp Gly
1               5                   10                  15

Leu Arg

<210> SEQ ID NO 3
<211> LENGTH: 7
<212> TYPE: PRT
<213> ORGANISM: Artificial Sequence
<220> FEATURE:
<223> OTHER INFORMATION: Peptide PE(22-28)

<400> SEQUENCE: 3

Gly Val Ser Trp Gly Leu Arg
1               5

<210> SEQ ID NO 4
<211> LENGTH: 15
<212> TYPE: PRT
<213> ORGANISM: Artificial Sequence
<220> FEATURE:
<223> OTHER INFORMATION: Peptide PE(13-27)

<400> SEQUENCE: 4

Pro Leu Pro Arg Trp Ser Gly Pro Ile Gly Val Ser Trp Gly Leu
1               5                   10                  15

<210> SEQ ID NO 5
<211> LENGTH: 12
<212> TYPE: PRT
<213> ORGANISM: Artificial Sequence
<220> FEATURE:
<223> OTHER INFORMATION: Peptide PE(14-25)

<400> SEQUENCE: 5

Leu Pro Arg Trp Ser Gly Pro Ile Gly Val Ser Trp
1               5                   10

<210> SEQ ID NO 6
<211> LENGTH: 9
<212> TYPE: PRT

```
<213> ORGANISM: Artificial Sequence
<220> FEATURE:
<223> OTHER INFORMATION: Peptide PI-PE(22-28)

<400> SEQUENCE: 6

Pro Ile Gly Val Ser Trp Gly Leu Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Peptide G/A-PE(22-28)

<400> SEQUENCE: 7

Ala Val Ser Trp Gly Leu Arg
1               5
```